Sept. 16, 1969 H. KERRIGAN Plant Pat. 2,918
AZALEA PLANT
Filed Dec. 21, 1967
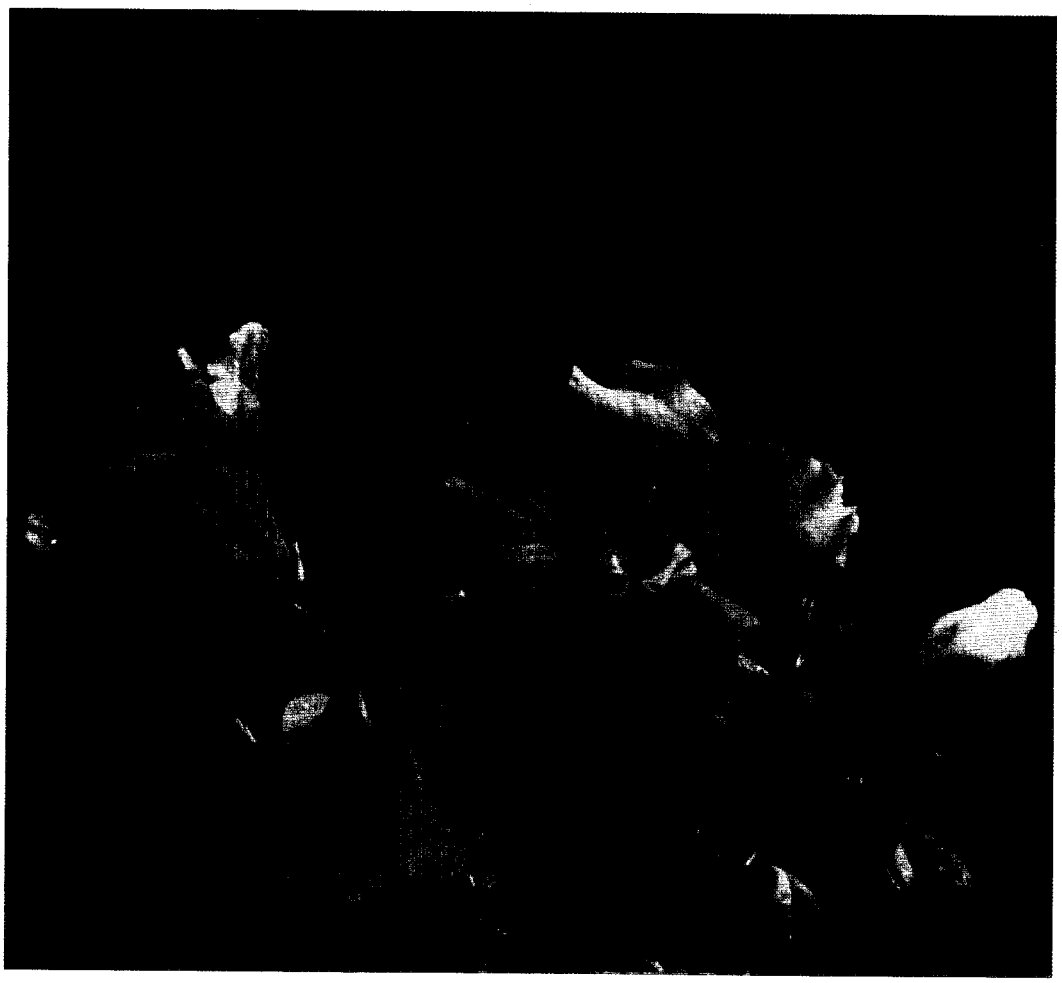

United States Patent Office

Plant Pat. 2,918
Patented Sept. 16, 1969

2,918
AZALEA PLANT

Howard Kerrigan, Oakland, Calif., assignor to Nurserymen's Exchange, Inc., a corporation of California Filed Dec. 21, 1967, Ser. No. 692,610
Int. Cl. A01h 5/02
U.S. Cl. Plt.—57 1 Claim The invention relates to a new and distinct variety of azalea plant of the Belgian Indica type, originated by me in 1952 as a consequence of a breeding program begun in 1943. The parentage of my new azalea plant is as follows:

L. C. Bobbink (P.P. No. 611 expired) the seed parent × Miss Cottage Gardens (unpatented) the pollen parent.

The object of the cross was to produce a Christmas forcing azalea of the Belgian Indica type with the uniform bud set and forcing habit of "Miss Cottage Gardens," but with a fuller petal form and clearer red color. These objectives were achieved along with other desirable improvements, as evidenced by the following unique combination of characteristics which are outstanding in the new variety and which distinguish it from its parents as well as from all other varieties of which I am aware. My new variety is primarily characterized by: the resemblence to the pollen parent, "Miss Cottage Gardens," in color, but conspicuous by its vast difference from either parent by having a much larger leaf, much larger flower and a much more rapid growth habit than either parent, its growth rate which resembles that of the variety "Redwing" (P.P. No. 1,159); its faster growth rate when compared to "Redwing" and its larger flower, longer flowering period and resistance to early flower drop.

Asexual production of my new variety by cuttings, through a series of annular propagations at Oakland and Santa Rosa, Calif., shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of my own rooted plants produced and grown under average conditions in greenhouses at Oakland and Santa Rosa, Calif. from 1954 to 1967.

Large, robust, ascending plant spreading 40–48 inches high and 30–36 inches across at maturity. Branches stout, but supple, gently arching. Basal shoots vigorous, about ⅛ inch in diameter; axillary branches about 3/32 inch the first season. Internodes of basal shoots between ⅛ inch to ⅝ inch long. Stems erect to slightly pendulous; rufous when young, becoming light green at the base and becoming rufous to brown when old. Bark more or less conspicuously striate, young stems bearing prominent hyaline to chestnut striga (becoming chestnut with age, i.e. located on basal portion of stem).

Foliage evergreen, of two size classes. Leaves of vigorous growth about 1½ to 1⅞ inches long by ¾ to 1⅛ inches wide, petiolate, the petiols about 5/16 inch long, lamina decurrent, descending the petiole up to ⅛", elliptic. The margin is entire, somewhat citiate, the cilia small, inconscicuous. The apex is acute. The midrib is pubescent, especially below. The trichomes are flat, lanceolate, slender up to 3/32" in length, conspicuous, hyaline, abundant on the lower surface, smaller, sparser, and hyaline on the upper surface of the midrib. The lamina is sparsely pubescent above and somewhat heavier below. Leaves of the branches from older wood smaller, about ¾–1⅛" long by ⅜–½" wide with proportionally smaller trichomes, but otherwise similar to the larger leaves. The color of the leaves is Spinach Green (HCC 0960) above and Spinach Green (HCC 0960/2) below.

The bud of the inflorescence is Pod Green (HCC 061). The scales are small, about ¼" wide x about ½" long, heart shaped to strap shaped becoming cucullate at anthesis. Pubescence is moderate to heavy, small, golden brown essentially restricted to the rib. The scales become scarious with sub-hyaline margins at dehiscence.

The inflorescence is 2–3 flowered. The flowers are borne in an umbellate corymb. One flower of three-flowered inflorescences matures several days later than the more precocious pair and has a shorter peduncle. The peduncles are short, stout 7/16–⅝" long x 3/32" wide, pubescent, light green to red (where exposed to sunlight). Pubescence moderately dense, hyaline to chestnut, where exposed to sunlight, with pink bases, short and silky. Calyx corolliform, sepals imperfect, ragged, 5 lobed. Tube of calyx about ¾" deep x ¾" across, broadly flared, lightly fluted, very irregular and fimbriate. Lobes from ¼"–¾" wide by ¾"–1¼" long or some lobes entirely missing; highly variable as to shape and size, secondarily lobed and incised. The margins of the lobes are long ciliate. The reverse of the calyx is splotched with China Rose (HCC 024/3) and is sparsely pubescent. Located between the calyx and coralla are from 1–4 coralline appendages from ⅜"–½" long. The coralla is China Rose (HCC 025) with freckles of Rose Red (HCC 724) on the tube of the standard. The reverse is Rose Red (HCC 724/2) on the coralla lobes and becoming Rose Red (HCC 724) on the tube. The calyx and appendages are the same color as the coralla. The tube is about 1⅛" long x 1 3/16" across at the throat, flaring bilaterally symetrical, slightly gibbous, somewhat higher than broad, more or less prominately fluted. The five coralla lobes are of two size classes, the ventral two larger about 1⅛"–1⅜" across by 1¼"–1½" long, undulate. The dosal 3 lobes are smaller, about 1⅛"–1¼" across by ⅞"–1" long. The flower is about 3–3½" across by 2–2¼" deep.

The stamens are five, filaments slender, China Rose (HCC 024), ¾"–1¾" long; the staminodia are petalacious and are 4–5 in number, they come in two sizes; the larger 2 measure about ½" wide and 2–2⅛" long, the smaller 2–3, measure about 3/16" wide by ⅝–¾" long. Anthers small, black, about 1/16" x 3/32" pollen white. The pistil is long, 1¼"–1½" long, stigma Rose Red (HCC 724), capitate, 5 lobed, receptive surface divided into 5 sections; style slender, 1¼" long (about), curved not sigmoid, not expanded at base. Ovary about 5/32" long by ⅛" across, heavily pubescent, the pubescence dense, long, silky, hyaline.

Having thus disclosed my invention, I claim:

1. A new and distinct variety of azalea plant of the Belgian Indica type substantially as herein shown and described primarily characterized by: the resemblance to the pollen parent, "Miss Cottage Gardens" in color, but conspicuous by its vast difference from either parent by having a much larger leaf, much larger flower, and a much more rapid growth habit than either parent; its growth rate which resembles that of the variety "Redwing" (P.P. No. 1,159); its faster growth rate when compared to "Redwing" and its larger flower, longer flowering period and resistance to early flower drop.

No references cited.

ROBERT E. BAGWILL, Primary Examiner